(12) United States Patent
Chalmers

(10) Patent No.: US 7,074,981 B2
(45) Date of Patent: Jul. 11, 2006

(54) WOUND DRESSINGS AND WOUND TREATMENT COMPOSITIONS

(76) Inventor: Susanna Elizabeth Chalmers, 31 Sarel Cilliers Street, Riebeeck-Kasteel, Western Cape Province 7307 (ZA)

( * ) Notice: Subject to any disclaimer, the term of this patent is extended or adjusted under 35 U.S.C. 154(b) by 242 days.

(21) Appl. No.: 10/477,770

(22) PCT Filed: May 2, 2002

(86) PCT No.: PCT/IB02/01480

§ 371 (c)(1), (2), (4) Date: Nov. 14, 2003

(87) PCT Pub. No.: WO02/091965

PCT Pub. Date: Nov. 21, 2002

(65) Prior Publication Data
US 2004/0138601 A1    Jul. 15, 2004

(30) Foreign Application Priority Data
May 16, 2001 (ZA) ................................. 2001/3975
Oct. 19, 2001 (ZA) ................................. 2001/8605

(51) Int. Cl.
*A61F 13/00* (2006.01)
*A61F 15/00* (2006.01)

(52) U.S. Cl. ............................ 602/41; 602/43; 602/47; 602/48; 602/56; 602/58

(58) Field of Classification Search ............ 602/41–43, 602/45, 47–51, 54–56; 424/443–449
See application file for complete search history.

(56) References Cited

U.S. PATENT DOCUMENTS 2,465,357 A * 3/1949 Correll ....................... 106/122
4,060,081 A * 11/1977 Yannas et al. ............ 623/15.12
4,265,233 A * 5/1981 Sugitachi et al. ............ 604/304
4,292,972 A * 10/1981 Pawelchak et al. ......... 604/368
4,360,015 A * 11/1982 Mayer .......................... 602/47
4,407,787 A * 10/1983 Stemberger ................. 424/444
4,427,650 A   1/1984 Stroetmann
4,499,896 A   2/1985 Heinecke
4,683,142 A * 7/1987 Zimmermann et al. .... 427/2.24
5,128,136 A * 7/1992 Bentley et al. ............. 424/443
5,227,168 A * 7/1993 Chvapil et al. ............. 424/445
5,244,457 A * 9/1993 Karami et al. ................ 602/55
5,466,231 A * 11/1995 Cercone et al. ............. 604/369
5,632,731 A * 5/1997 Patel ........................... 602/59
5,723,145 A * 3/1998 Shikinami et al. .......... 424/448

(Continued)

FOREIGN PATENT DOCUMENTS

EP    0 601 835    6/1994

(Continued)

*Primary Examiner*—Henry Bennett
*Assistant Examiner*—Amanda Wieker
(74) *Attorney, Agent, or Firm*—Meyertons, Hood, Kivlin, Kowert & Goetzel, P.C.; Eric B. Meyertson

(57) ABSTRACT

In various embodiments, a wound dressing includes a wound treatment composition including at least one absorbent or adsorbent compound contained within a sheath having an operatively inner and an operatively outer wall. A surface of the operatively inner wall of the wound dressing, that is to contact a wound in use, is a substantially smooth continuous surface conveniently of a plastic inner wall, selected for easy release from a wound. The inner wall is perforated to enable exudates or slough to pass therethrough. In some embodiments, a wound treatment composition includes an absorbent material, preferably silica, for adsorbing moisture on or around a wound and a collagen, conveniently gelatin.

20 Claims, 2 Drawing Sheets

U.S. PATENT DOCUMENTS 5,800,372 A     9/1998   Bell et al.
6,191,335 B1    2/2001   Robinson
6,486,378 B1 *  11/2002  Areskoug et al. ............ 602/41
6,573,419 B1 *  6/2003   Naimer ........................ 602/41
6,592,885 B1 *  7/2003   Phaneuf et al. ............. 424/404

2001/0028894 A1 * 10/2001 Gueret ...................... 424/443
2004/0241215 A1 * 12/2004 Lipman ..................... 424/445

FOREIGN PATENT DOCUMENTS

WO     WO-00/09176     2/2000

* cited by examiner

WOUND DRESSINGS AND WOUND TREATMENT COMPOSITIONS

FIELD OF THE INVENTION

This invention relates, in the first place, to wound dressings and, more particularly, to wound dressings of the general type comprising an absorbent or adsorbent composition, optionally together with one or more other compounds, generally in powder or granular form, and contained within a sachet made of a moisture permeable material. Such wound dressings may contain a variety and even a combination of different absorbent or adsorbent compositions the object of which is to absorb or adsorb exudate from a wound and thereby assist in, and generally accelerate, the healing process. The healing process may also be assisted by said one or more other compounds. The invention is particularly concerned, although not exclusively, with wound dressings that are suitable for the treatment of relatively large wounds and areas of skin.

The invention also relates to a wound treatment composition that can be used in different forms but is preferably used in a wound dressing, in particular one according to this invention. In this respect, the invention relates more particularly to a composition of the general type described in my earlier South African Patent No 93/9117 and its European counterpart namely European Patent application publication number EP-0601835 as well as in my later international patent application publication number WO-00/09176. As indicated above, such wound treatment compositions can be used to encourage the more rapid healing of wounds.

BACKGROUND TO THE INVENTION

Wound dressings of the type outlined above that have been used in the past invariably have a woven or non-woven fibrous sheet of material forming the surface of the dressing that actually contacts the wound in use.

The disadvantage of this arrangement is that there is a distinct tendency for the fibrous sheet of material to become stuck to the wound and this can have a seriously deleterious effect when the time arrives to remove the dressing. Indeed, a patient can be subjected to substantial pain during the removal process and a considerable amount of good that has been achieved as regards the healing process can be lost. This situation is generally not improved by interposing a layer of lint, or other fibrous material, typically a fabric pad or the like, between the wound and the dressing as the lint or fibres of the pad can then become stuck to the wound. In addition, in such a removal process granulation tissue can be destroyed and this generally retards the healing process.

Reverting now to the treatment compositions, in my said earlier patent applications I describe wound treatment compositions that are composed of two basic ingredients, namely, an anti-septic or antimicrobial agent and a desiccant by which term is meant a compound operating on the basis of adsorption rather than one of absorption. The preferred compositions have included sodium chloride or sucrose as the antimicrobial agent, and silica gel as the desiccant.

Whilst these compositions operate effectively from a medical and thus healing point of view they have certain disadvantages from the point of view that the sodium chloride or sucrose tends to become dissolved to some extent in the moisture being adsorbed. As a consequence the sodium chloride or sucrose can tend to migrate through the moisture permeable membrane that generally forms part of an envelope containing the composition and which is supposed to form a barrier between the composition and the wound itself. The consequence of this is that, in the case of sodium chloride, the patient suffers considerable pain in consequence of sodium chloride entering the wound. In both cases there has also been a tendency for the composition to stick to the wound to some extent thereby causing difficulties in removal of the dressing and this represents another possible source of pain to the patient.

Collagen is widely used as a direct wound treatment composition. Numerous different methods and vehicles for Its application to wounds have been proposed and used such as application directly to the wound in particulate form; in the form of a suspension; in the form of a gel, optionally in combination with other active ingredients such as iodine; as an exposed layer in the central area of an adhesive dressing; and as an active ingredient of a spray for application to a wound.

Prior U.S. Pat. No. 5,800,372 discloses a field dressing in which collagen is used to promote blood clotting in fresh wounds in order to stem the bleeding and propagate blood clotting backwards towards the wound. The collagen is mixed with a super absorbent polymer that serves to absorb a large quantity of liquid contained in the blood.

It has now surprisingly been found that the beneficial effects of collagen can be exploited in what applicant believes to be a novel and surprisingly effective manner.

OBJECT OF THE INVENTION

It is accordingly ones object of this invention to provide a wound dressing that is adapted to release more easily from a wound than prior art dressings described above. It is another object of the invention to provide a wound treatment composition in which the drawbacks associated with my earlier wound treatment compositions as outlined above are diminished, at least to some extent.

SUMMARY OF THE INVENTION

In accordance with one aspect of this invention there is provided a wound dressing comprising a wound treatment composition including at least one absorbent or adsorbent compound in the form of a silica gel contained within a sheath having an operatively inner wall (5) perforated (7) to enable exudate or slough to pass therethrough and an operatively outer wall, the wound dressing being characterized in that the silica gel has admixed therewith a collagen.

Further features of the invention provide for the surface of the operatively inner wall that is to contact a wound in use to be a substantially smooth continuous plastics surface, typically the exposed surface of a plastics operatively inner wall to the sheath; for the operatively inner wall of the sheath to be a film of medical grade of polypropylene or other suitable plastics material having a thickness of from about 15 micron to about 180 micron with, for example, strike through perforations; for the operatively outer wall of the sheath to be a perforated plastics film, conveniently polyethylene, to which there is preferably bonded a layer of highly absorbent material such as a fluff pulp tissue having a weight of about 40 to about 180 grams per square metre; and for the wound treatment composition to be contained in one or more prefabricated permeable sachets thereof one or more of which is or are located within the sheath.

The moisture permeable material of the sachet is preferably a non-woven fibrous polypropylene material having a weight of from 15 to 60 grams per square metre such as that used for manufacturing tea bags, or alternatively, a cellulosic material.

It is preferred that the sheaths be produced in a form in which each sheath is interconnected with a series of adjacent sheaths to form a succession of rows of sheaths interconnected by regions of sheet material forming the inner and outer walls of the sheaths and wherein such regions are welded together, typically by thermal welding, at least along predetermined lines to define the peripheral boundaries to each sheath. Preferably the thermal welding is effected along two parallel lines spaced apart to define a zone of sheet material in between the sheaths themselves and along which one sheath, or a particular series of sheaths, can be severed by cutting or tearing along predetermined lines of weakening, said zone between the two parallel welds. Of course, the sheath does not have to be formed by welding the two sheets together and they could equally well be stitched, glued or otherwise secured together.

From a structural integrity point of view additional layers of sheet material may be added in order to facilitate thermal welding and with this end in view a non-woven fibrous sheet could be interposed between the operatively inner wall that provides the substantially continuous surface for contacting the wound and the absorbent or adsorbent compound and a similar layer could be provided on the outside of the outer wall so that those two similar layers can be thermally bonded together effectively to ensure integrity with the inner wall being attached to the composite structure.

Preferably, the wound treatment composition is one that is provided in accordance with the second aspect of this invention defined below. Nevertheless, this first aspect of the invention extends to other wound dressing compositions and in particular other absorbent and adsorbent materials. The absorbent or and adsorbent material may thus, for example, be a subdivided porous ceramic material that is presently being marketed in a different type of wound dressing having the form of a simple sachet of permeable fibrous sheet material.

In accordance with a second aspect of the invention there is provided a wound treatment composition comprising, in combination:

(a) silica gel for adsorbing moisture on or around a wound; and,
(b) a collagen.

The collagen can be any medically acceptable collagen and it has been found that conventional food grade of gelatin operates effectively. The proportions of the adsorbent material to the collagen can wary widely but preferably, as far as, applicant can establish at the present time, the proportions in the case of gelatin and silica gel are about 10 to 15% by weight of gelatin to about 85 to 90% by weight of silica gel.

The wound treatment composition may also contain an indicator that changes in a visible physical characteristic, in particular its colour, in the presence of moisture to indicate moisture saturation of the wound treatment composition and, accordingly, the necessity for changing it. The indicator may be cobaltous chloride ($CoCl_2$) which is blue in its anhydrous form, but which turns pink when hydrated. The cobaltous chloride is typically present in an amount of about 0.5% by weight of the wound treatment composition. Conveniently, the cobaltous chloride can be chemically bonded to a portion of the silica gel that then has the formula $SiOCoCl_2$ as opposed to the formula $SiO_2$ applicable in respect of the balance of the silica gel. In such an instance the cobalt containing silica gel may comprise about 1% of the total silica gel.

The invention also provides a wound dressing comprising a quantity of wound treatment composition as defined above contained within a sheath or sachet as defined above.

The sachet or sheath is generally substantially flat but it may be made to any shape such as that of an elongate plug for insertion into a wound. In the case of a plug or similar shape, the wound dressing may comprise a gripping formation optionally in the form of a tab attached, for example, to one end of the plug and optionally formed integral with the sachet or sheath.

According to another aspect of the invention a wound treatment kit is provided comprising a wound treatment composition according the invention, generally in the form of one or more sachets or sheaths containing same, and separate attachment means for maintaining the wound treatment composition in contact with a wound.

In order that the invention may be more fully understood, the implementation thereof will now be further described and exemplified with reference to the accompanying drawings.

DETAILED DESCRIPTION WITH REFERENCE TO THE DRAWINGS

Various preferred forms of wound dressings according to the invention and the preferred wound treatment composition will now be described.

In this embodiment of wound treatment composition, the composition comprises a dry mixture made up of 615 parts by weight (about 88% by weight) of silica gel ($SiO_2$); 6 parts by weight (about 1% by weight) moisture indicating silica gel having attached to this silica gel cobaltous chloride indicator ($SiOCoCl_2$); and 79 parts by weight (about 11% by weight) of food grade of gelatin as a collagen.

Figure 1:
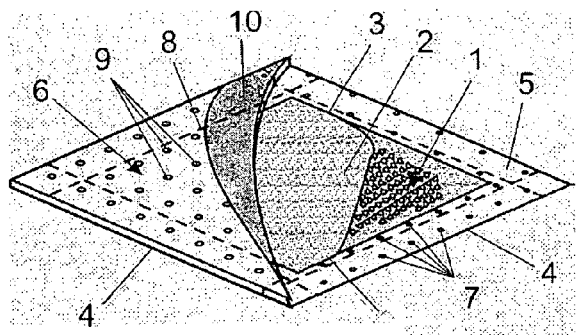
FIG. 1 is a schematic perspective view of one preferred wound dressing according to the invention showing the construction by way of cut away portions of the various layers.
Figure 3:
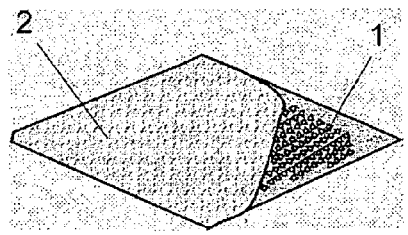
FIG. 3 is a schematic perspective view illustrating a single sachet containing wound dressing composition and that may be used inside the sheath of the wound dressing illustrated in FIG. 1.

This wound treatment composition, indicated by numeral (1), is pre-packaged in sachets (2), as illustrated in FIGS. 1 and 3, that are heat sealed around the periphery as indicated by numeral (3) so that the particulate solid material (1) becomes enclosed in a highly permeable sheet material sachet. This sheet material can be of the same type as that of which tea bags are commonly made and, particularly, may be a non-woven fibrous polypropylene material having a weight of from 15 to 60 grams per square metre.

In the broad application of the wound dressing composition of this invention, the sachets described above can be employed directly on a wound, although by so doing, the difficulties associated with prior art wound dressings that are outlined above could be experienced. Accordingly, it is preferred that the wound dressing composition be employed in the wound dressings provided by this invention.

To this end the prefabricated sachets are sandwiched between sheets of material that will be described below so as to form a sheath around the sachet (or in the event that more than one sachet is embodied in a single sheath, the sachets).

In one embodiment of the invention, two sheets of material form the sheath as illustrated in FIG. 1, and the sheets are thermally welded together adjacent the edges (4) of the sheath to enclose the sachet of wound treatment composition. These two sheets of material are different from each other and the one forming the operatively inner wall of the sheath (that is to say the one in contact with the wound) is indicated by numeral (5), and that on the operatively outer side remote from the wound defines a composite wall that is indicated by numeral (6).

The inner wall (5) consists of a continuous film of smooth plastics material, conveniently medical grade of polypropylene, that is rendered moisture permeable by the provision of a multitude of holes (7). The thickness of this film can range from 15 microns to 180 microns, and is preferably about 20 microns thick.

The outer wall (6) consists of a bonded composite sheet of material having an outer layer (8) of low density polyethylene with pinhole perforations (9) to provide the wall with the ability to breath to an adequate extent. The inner layer (10) is made of an absorbent cellulose fluff pulp with a binder to provide it with adequate integrity. The inner layer can range from between 40 to 80 grams is square metre.

In use, it has been found that a wound dressing made as described above is highly effective and does not tend to stick to a wound when the polypropylene film is contacted with the wound. The perforations through the film are adequate to enable exudate to pass through the otherwise impermeable film and to become adsorbed onto the silica with excess being absorbed by the absorbent fluff pulp layer.

Figure 4:
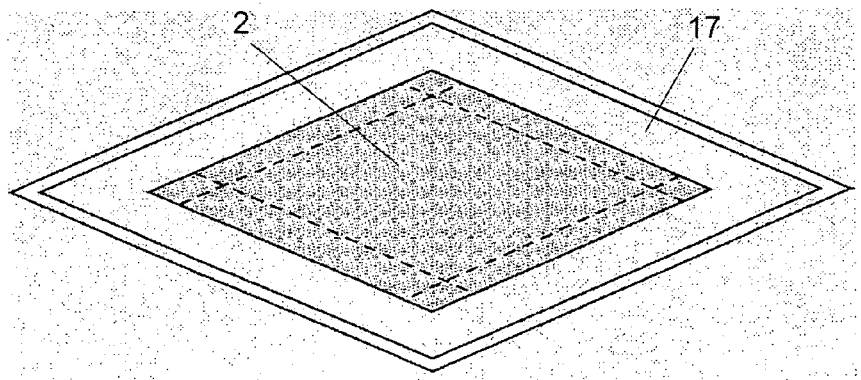
FIG. 4 is a schematic perspective view illustrating a packaged wound dressing of the type illustrated in FIG. 1; and, FIGS. 5 to 9 each illustrates one of a series of different forms in which wound dressings according to the invention can be manufactured, packaged and supplied.

As shown in FIG. 4, a wound dressing of the type described above may be packaged for distribution within a protective sealed outer wrapping (17) and may be sterilized after they are wrapped in known manner, for example by gamma radiation.

Figure 2:
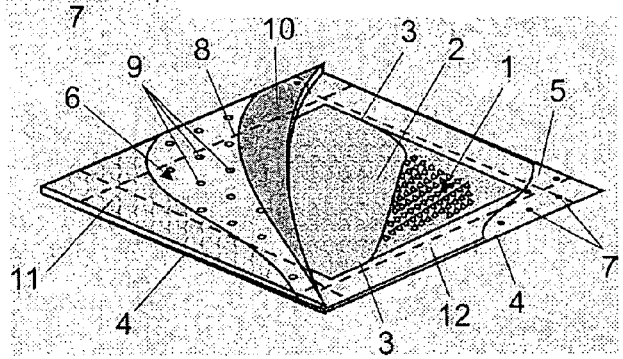
FIG. 2 is a similar schematic perspective view showing an alternative construction adapted to provide additional integrity to the composite dressing.

Because of the different type of material of which the inner and outer layers are made, it may be considered desirable, in order to ensure the integrity of the sheath enclosing the sachets, and as illustrated in FIG. 2, to add two like, non-woven highly permeable fibrous sheets (11) and (12) to enclose the wound treatment composition. These sheets could typically be fibrous polypropylene sheets. The one additional sheet (11) can be located on the outside of the operatively outer wall (6) and the other one (12) between the operatively inner wall (5) and the sachet. These two like plastics sheets would weld particularly effectively together to ensure effective entrapment of the wound treatment composition and the operatively inner wall (5) can be welded or otherwise attached to the resultant construction.

The wound dressings of this invention are conveniently produced in large sheets by locating, and preferably attaching either by "spot" welding, although means of adhesive, the prefabricated sachets in position, conveniently on the composite sheet, and thermally welding the inner and outer sheets together along spaced parallel lines indicated by numeral (13) in FIGS. 4 to 7 between the positions where the sachets are located. This leaves a narrow zone (14) of the sheets between the parallel lines and along which the sheets can be severed to produce usable sizes of wound dressings.

It is also envisaged that the zones (14) of the sheaths between the parallel lines of thermal welding could be suitably weakened to enable severing to take place by tearing thereby avoiding the necessity of utilizing a pair of scissors. However, these zones are preferably not perforated in order to facilitate separation of adjacent sheaths and sachets in order to preserve the generally waterproof characteristics of the wound dressing and to prevent exudate from leaking to the outer surface.

It will therefore be understood that the wound dressings of this invention may be supplied in numerous different configurations, a few examples of which will now be described with reference to FIGS. 5 to 9 of the drawings.

Figure 5:
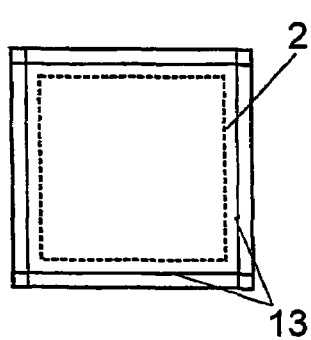

FIG. 5 illustrates a wound dressing consisting of a sheath enclosing a single sachet of wound dressing composition (as described above) for use in the treatment of small wounds.

Figure 6:
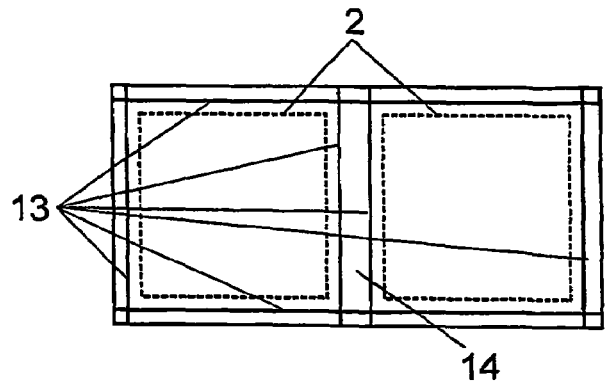

The wound dressing illustrated in FIG. 6 consists of two sheaths still interconnected by a zone (14) of the sheets of material.

Figure 7:
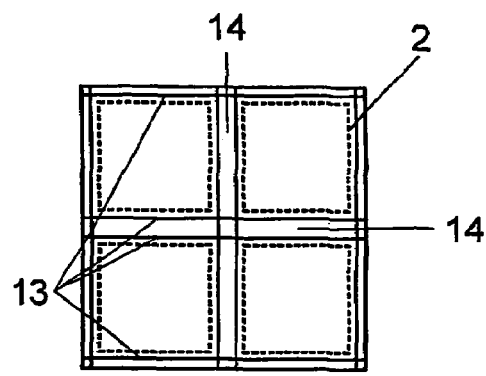
Figure 8:
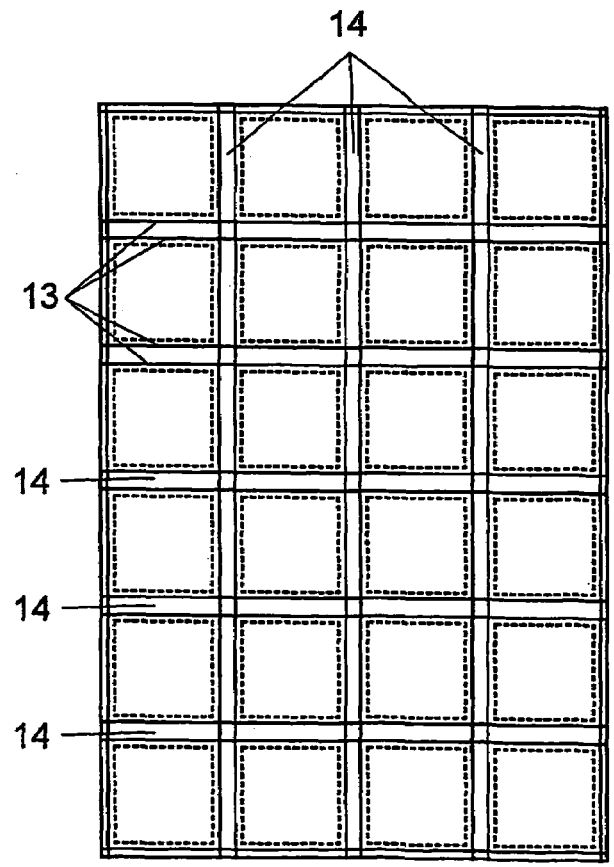

FIG. 7 illustrates a larger dressing consisting of four sheaths and enclosed sachets whilst FIG. 8 illustrates a match larger dressing consisting of twenty interconnected sheaths and sachets that can be particularly useful in the treatment of injuries extending over large surface areas of skin such as burns.

Figure 9:
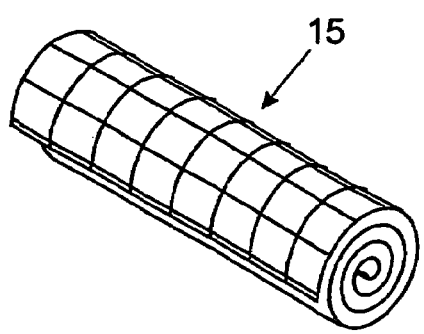

FIG. 9 illustrates a still further form in which the wound dressing of the invention is supplied in a roll form (15) that can be cut or severed along the zones between adjacent sheaths and sachets to form any size of wound dressing that may be required for any particular application.

It will be understood that numerous variations may be made to the embodiments of the invention described above without departing from the scope hereof.

In particular, as indicated above, the sachets could be used directly in various different ways without enclosing them in sheaths as described above. In particular, for example, a plurality of sachets of the type illustrated in FIG. 3 may be adhered to a support layer. The support layer may also be made of a non-woven material and may have a plastics moisture impermeable layer.

This moisture impermeable backing layer is important in that it isolates the sachets from the surrounding atmosphere, which contains a certain amount of moisture, and thus prevents this moisture from adsorbing onto the silica gel. However, the advantages of the substantially continuous surface of the sheath are absent in this application of the wound dressing compositions of the invention.

The wound dressings of the invention may also be packaged in a kit form for out-patient use. Such a kit may contain any dressing of the invention. The components of the kit are typically placed in a moisture proof polymeric plastics bag to maintain dryness and sterility of the wound dressing and wound treatment composition. Where appropriate a separate attachment means for maintaining the wound dressing in contact with the wound will also need to be provided as a part of the kit.

In use, the wound dressings are applied to a wound in the usual manner with one of the permeable walls of the sachet in contact with the wound. The effect achieved using the two basic components has been found to be somewhat remarkable. The silica gel that, on its own is believed to be too aggressive for practical use, nevertheless serves to adsorb exudate rapidly and effectively from a wound. It is considered by applicant that the effective withdrawal of such exudates is critical to rapid healing.

On the other hand, the collagen, which applicant finds too slow in acting on its own, serves the purpose of receiving and killing bacteria effectively. The combined effect of the two major components is apparently synergistic in that wounds heal at a significantly enhanced rate.

Typically, a wound dressing of the invention is replaced at regular intervals, for example every 4 to 6 hours, or in some cases daily, depending on the state of the wound.

It will be understood that numerous variations and permutations of wound treatment composition and dressing are possible within the scope of the invention without departing from the scope hereof.

The invention claimed is:

1. A wound dressing comprising a wound treatment composition including at least one absorbent or adsorbent compound in the form of silica gel contained within a sheath having an operatively inner wall perforated to enable exudates or slough to pass therethrough and an operatively outer wall of perforated plastics film to which there is bonded a layer of highly absorbent material and wherein collagen is admixed with the silica gel.

2. A wound dressing as claimed in claim 1 in which the surface of the operatively inner wall that is to contact a wound in use is a substantially smooth continuous plastics surface of a plastic inner wall.

3. A wound dressing as claimed in claim 2 in which the inner wall of the sheath is a film of medical grade polypropylene or other suitable plastics material.

4. A wound dressing as claimed in claim 1 in which the wound treatment composition is contained in one or more prefabricated moisture permeable sachets thereof located within the sheath.

5. A wound dressing as claimed in claim 4 in which the moisture permeable material of the sachet is a non-woven fibrous polypropylene material.

6. A wound dressing as claimed in claim 1 in which the collagen is gelatin.

7. A wound dressing comprising a wound treatment composition comprising at least one absorbent or adsorbent compound in the form of silica gel contained within a sheath having an operatively inner wall perforated to enable exudates or slough to pass therethrough and an operatively outer wall and wherein collagen is admixed with the silica gel, and wherein the sheaths are produced in a form in which each sheath is interconnected with a series of adjacent sheaths to form a succession of rows of sheaths interconnected by regions of sheet material forming the inner and outer walls of the sheaths and wherein such regions are welded together at least along predetermined lines to define the peripheral boundaries to each sheath.

8. A wound dressing as claimed in claim 7 in which the surface of the operatively inner wall that is to contact a wound in use is a substantially smooth continuous plastics surface of a plastic inner wall.

9. A wound dressing as claimed in claim 7 in which the inner wall of the sheath is a film of medical grade polypropylene or other suitable plastics material.

10. A wound dressing as claimed in claim 7 in which the operatively outer wall of the sheath is a perforated plastics film to which there is bonded a layer of highly absorbent material.

11. A wound dressing as claimed in claim 7 in which the wound treatment composition is contained in one or more prefabricated moisture permeable sachets thereof located within the sheath.

12. A wound dressing as claimed in claim 11 in which the moisture permeable material of sachet is a non-woven fibrous polypropylene material.

13. A wound dressing as claimed in claim 7 in which the collagen is gelatin.

14. A wound dressing comprising a wound treatment composition comprising at least one absorbent or adsorbent compound in the form of silica gel contained within a sheath having an operatively inner wall perforated to enable exudates or slough to pass therethrough and an operatively outer wall and wherein collagen is admixed with the silica gel, and wherein the sheaths are produced in a form in which each sheath is interconnected with a series of adjacent sheaths to form a succession of rows of sheaths interconnected by regions of sheet material forming the inner and outer walls of the sheaths and wherein such regions are welded together at least along two parallel lines spaced apart to define a zone of sheet material in between the sheaths themselves and along which the sheaths can be severed from each other.

15. A wound dressing as claimed in claim 14 in which the surface of the operatively inner wall that is to contact a wound in use is a substantially smooth continuous plastics surface of a plastic inner wall.

16. A wound dressing as claimed in claim 14 in which the inner wall of the sheath is a film of medical grade polypropylene or other suitable plastics material.

17. A wound dressing as claimed in claim 14 in which the operatively outer wall of the sheath is a perforated plastics film to which there is bonded a layer of highly absorbent material.

18. A wound dressing as claimed in claim 14 in which the wound treatment composition is contained in one or more prefabricated moisture permeable sachets thereof located within the sheath.

19. A wound dressing as claimed in claim 18 in which the moisture permeable material of sachet is a non-woven fibrous polypropylene material.

20. A wound dressing as claimed in claim 14 in which the collagen is gelatin.

* * * * *